United States Patent
Gattupalli et al.

(10) Patent No.: US 10,246,385 B2
(45) Date of Patent: Apr. 2, 2019

(54) INTEGRATED PYROLYSIS AND OXYGENATE TO OLEFIN PROCESS

(71) Applicant: UOP LLC, Des Plaines, IL (US)

(72) Inventors: Rajeswar R. Gattupalli, Buffalo Grove, IL (US); Andrea G. Bozzano, Northbrook, IL (US); Laura E. Leonard, Western Springs, IL (US); Gregory A. Funk, Carol Stream, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 15/846,550

(22) Filed: Dec. 19, 2017

(65) Prior Publication Data

US 2018/0111886 A1    Apr. 26, 2018

Related U.S. Application Data

(63) Continuation of application No. PCT/US2016/036564, filed on Jun. 9, 2016.
(Continued)

(51) Int. Cl.
*C07C 5/09* (2006.01)
*B01J 19/10* (2006.01)
(Continued)

(52) U.S. Cl.
CPC ............. *C07C 5/09* (2013.01); *B01J 19/10* (2013.01); *C07C 1/12* (2013.01); *C07C 1/20* (2013.01);
(Continued)

(58) Field of Classification Search
CPC ......... C07C 1/12; C07C 1/20; C07C 29/1518; C07C 2/78; C07C 5/09; C10G 2400/20; C10G 2400/22; C10G 2300/1081; C10G 2300/1088; C10G 29/205; C10G 29/22; C10G 3/60; C10G 45/34; C10G 45/40; C10G 57/00; C10G 69/06; B01J 29/85;
(Continued)

(56) References Cited

U.S. PATENT DOCUMENTS 3,326,956 A    6/1967 Phineas et al.
3,928,483 A    12/1975 Chang et al.
(Continued)

FOREIGN PATENT DOCUMENTS

GB    921305 A    3/1963
GB    958046 A    5/1964
(Continued)

OTHER PUBLICATIONS

Search Report dated Oct. 6, 2016 for corresponding PCT Appl. No. PCT/US2016/036564.

*Primary Examiner* — Sharon Pregler

(57) ABSTRACT

A method of making light olefins is described. The method involves producing an alkyne in a pyrolysis process. The alkyne is catalytically hydrogenated in a hydrogenation zone to produce a product stream containing a light olefin. A byproduct stream from the pyrolysis process comprises carbon oxide and hydrogen. The byproduct stream is treated to convert the carbon oxide and the hydrogen to an oxygenated product in a carbon oxide conversion zone, which can then be converted to an olefin in an oxygenate to olefin process.

16 Claims, 3 Drawing Sheets

Related U.S. Application Data

(60) Provisional application No. 62/183,314, filed on Jun. 23, 2015.

(51) Int. Cl.
| | | |
|---|---|---|
| *C07C 29/151* | (2006.01) | |
| *C07C 31/04* | (2006.01) | |
| *C07C 2/78* | (2006.01) | |
| *C07C 7/11* | (2006.01) | |
| *C10G 45/32* | (2006.01) | |
| *C10G 3/00* | (2006.01) | |
| *C07C 1/12* | (2006.01) | |
| *C07C 1/20* | (2006.01) | |
| *C07C 27/12* | (2006.01) | |

(52) U.S. Cl.
CPC .................. *C07C 2/78* (2013.01); *C07C 7/11* (2013.01); *C07C 27/12* (2013.01); *C07C 29/151* (2013.01); *C07C 29/1518* (2013.01); *C07C 31/04* (2013.01); *C10G 3/00* (2013.01); *C10G 45/32* (2013.01)

(58) Field of Classification Search
CPC ... B01J 19/26; B01J 23/44; B01J 23/50; B01J 23/52; B01J 23/60; B01J 21/04
See application file for complete search history.

(56) References Cited

U.S. PATENT DOCUMENTS

| | | | |
|---|---|---|---|
| 4,025,575 A | 5/1977 | Chang et al. | |
| 4,252,479 A | 2/1981 | Scherfenberg | |
| 4,447,669 A | 5/1984 | Hamon et al. | |
| 4,496,786 A | 1/1985 | Santilli et al. | |
| 4,499,314 A | 2/1985 | Seddon et al. | |
| 4,547,616 A | 10/1985 | Avidan et al. | |
| 4,677,242 A | 6/1987 | Kaiser | |
| 4,843,183 A | 6/1989 | Inui | |
| 4,861,938 A | 8/1989 | Lewis et al. | |
| 4,973,792 A | 11/1990 | Lewis et al. | |
| 5,095,163 A | 3/1992 | Barger | |
| 5,126,308 A | 6/1992 | Barger et al. | |
| 5,191,141 A | 3/1993 | Barger et al. | |
| 5,789,644 A | 8/1998 | Paessler et al. | |
| 5,824,834 A | 10/1998 | Bachtler et al. | |
| 5,847,250 A | 12/1998 | Flick et al. | |
| 6,797,851 B2 * | 9/2004 | Martens ................... | C07C 1/20 585/639 |
| 7,208,647 B2 | 4/2007 | Peterson et al. | |
| 7,396,972 B2 * | 7/2008 | Van Egmond ............ | C01B 3/36 518/704 |
| 8,829,259 B2 | 9/2014 | Bozzano et al. | |
| 8,921,632 B2 | 12/2014 | Montalbano et al. | |
| 8,992,738 B2 * | 3/2015 | Gafney ..................... | C07C 1/12 204/157.15 |
| 2005/0048658 A1 | 3/2005 | Johnson et al. | |
| 2005/0049445 A1 | 3/2005 | Johnson et al. | |
| 2007/0049647 A1 | 3/2007 | Van Egmond et al. | |
| 2007/0155999 A1 | 7/2007 | Pujado et al. | |
| 2011/0112345 A1 | 5/2011 | Chewter et al. | |
| 2014/0058149 A1 * | 2/2014 | Negiz ..................... | B01J 19/10 585/254 |
| 2014/0058179 A1 | 2/2014 | Stevens et al. | |
| 2014/0187833 A1 | 7/2014 | Chewter et al. | |

FOREIGN PATENT DOCUMENTS

| | | |
|---|---|---|
| WO | 2005035689 A2 | 4/2005 |
| WO | 2014005998 A1 | 1/2014 |

\* cited by examiner

INTEGRATED PYROLYSIS AND OXYGENATE TO OLEFIN PROCESS

CROSS-REFERENCE TO RELATED APPLICATIONS

This application is a Continuation of copending International Application No. PCT/US2016/036564 filed Jun. 9, 2016 which application claims benefit of U.S. Provisional Application No. 62/183,314 filed Jun. 23, 2015, the contents of which cited applications are hereby incorporated by reference in their entirety.

BACKGROUND OF THE INVENTION

Ethylene and propylene (light olefins) are commercially important chemicals. Ethylene and propylene are useful in a variety of processes for making plastics and other chemical compounds.

One important source of light olefins is based on the pyrolysis, e.g., the steam and catalytic cracking, of selected petroleum feed materials. These procedures also produce significant quantities of other hydrocarbon products.

Converting light hydrocarbons such as methane to high value olefins such as ethylene is very economically attractive. In conventional pyrolysis processes, some of the feed methane is burned to achieve temperatures high enough to convert the methane, but yielding low carbon efficiency due to inefficient control of the reaction time.

In conventional processes, methane can be converted to acetylene using either a one- or two-step process. An example of a one-step partial oxidation process developed by BASF is described in U.S. Pat. Nos. 5,824,834 and 5,789,644. The general reactor configuration and design are described in U.S. Pat. No. 5,789,644. Acetylene can also be produced using two-stage high temperature pyrolysis, and an example two stage reactor developed by HOECHST is described in Great Britain Patent Application Publication Nos. GB 921,305 and GB 958,046.

In conventional processes, an air separation unit can be used to separate oxygen from nitrogen. The oxygen or an oxygen containing stream, along with natural gas (composed primarily of methane), are preheated and enter a partial oxidation reactor. In the BASF one stage reactor, the hydrocarbon feed and oxygen rich gas are mixed and passed through a burner block which is used to stabilize the flame that results in partial oxidation of the mixture. Secondary oxygen can be injected at the burner block to create pilot flames. The burning converts approximately one-third of the methane to acetylene, while most of the remainder is used to produce heat and lower valued products such as CO and $CO_2$. The residence time required for the reaction process is less than 100 milliseconds. In the two stage reactor, natural gas or other fuel is mixed with an oxygen rich stream and burned in a combustion zone. The combustion products are then mixed with a feedstock of natural gas or other hydrocarbons which react to form acetylene. Again, a reaction time of less than 100 milliseconds is used. After the desired residence time, the reacting gas is quenched with water. The cooled gas contains large amounts of carbon monoxide and hydrogen as well as some carbon soot, carbon dioxide, acetylene, methane, and other gases.

Next, the gas passes through a water scrubber to remove the carbon soot. The gas then passes through a second scrubber in which the gas is sprayed with a solvent, such as N-methylpyrrolidone, which absorbs the acetylene.

The solvent is then pumped into a separation tower, and the acetylene is boiled out of the solvent and removed at the top of the tower as a gas, while the solvent is drawn out of the bottom.

The acetylene can be used to make a variety of useful products. One such product is ethylene, which can be produced by catalytically hydrogenating acetylene. A process for hydrogenating acetylene to ethylene in the presence of a $Pd/Al_2O_3$ catalyst is described in U.S. Pat. No. 5,847,250. A process for hydrogenating acetylene over a palladium-based catalyst using a liquid solvent, such as N-methylpyrrolidone, is described in U.S. Patent Application Publication Nos. 2005/0048658 and 2005/0049445.

Other known processes for converting methane to ethylene can be found in U.S. Pat. No. 7,208,647 to Synfuels International.

Controlling the reaction time is important to improve the carbon efficiency of the methane pyrolysis process. As such, technology to improve carbon efficiency is desired. Also, in addition to the main product acetylene, methane pyrolysis produces a large amount of byproducts such as carbon monoxide, hydrogen, carbon dioxide, and other gases. The economics of the process can be highly dependent on proper utilization of these byproducts.

Another, more recent source of light olefins is the oxygenate to olefins conversion process, and specifically the methanol-to-olefins (MTO) process. The MTO process is more effective in producing light olefins than conventional hydrocarbon pyrolysis systems. Instead of using a hydrocarbon source, this process is based on converting an oxygenate, such as methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof, and preferably methanol to olefins in the presence of a molecular sieve catalyst.

There is a need for a more efficient ways to produce greater yields of light olefins, and especially propylene, from hydrocarbon feed materials.

SUMMARY OF THE INVENTION

One aspect of the invention is a method of making light olefins. In one embodiment, the method includes combusting a fuel and an oxidizer in a combustion zone of a pyrolytic reactor to create a combustion gas stream. The velocity of the combustion gas stream is transitioned from subsonic to supersonic in an expansion zone of the pyrolytic reactor. A light hydrocarbon is injected into the supersonic combustion gas stream to create a mixed stream including the light hydrocarbon. The velocity of the mixed stream is transitioned from supersonic to subsonic in a reaction zone of the pyrolytic reactor to produce a reaction mixture comprising an alkyne, carbon oxide, and hydrogen. The reaction mixture is separated in an absorber into an alkyne stream comprising the alkyne and a byproduct stream comprising the carbon oxide and the hydrogen. The alkyne is catalytically hydrogenated in a hydrogenation zone to produce a product stream containing a first light olefin. The byproduct stream is treated to convert at least a portion of the carbon oxide and the hydrogen to an oxygenated product in a carbon oxide conversion zone. In some embodiments, the oxygenated product is treated in an oxygenate conversion zone to convert at least a portion of the oxygenated product to produce an effluent comprising a second light olefin.

DETAILED DESCRIPTION OF THE INVENTION

The methane pyrolysis process uses a supersonic reactor to convert methane to acetylene at very high temperatures. The reactor effluent contains mainly acetylene, hydrogen, carbon oxides, water and some heavier compounds. The water is removed in a quench tower before the cracked gases are sent to a compressor. The compressed gas is sent to an absorption unit to absorb the acetylene in a solvent. The acetylene is then hydrogenated to produce ethylene. The compressed gas which is not absorbed contains mainly carbon monoxide and hydrogen gas (synthesis gas).

The methane pyrolysis process has better economics when the synthesis gas byproduct is converted to a useful product. One method of doing this is to convert the synthesis gas into an oxygenate, followed by conversion of the oxygenate to olefins in an oxygenate to olefin process.

In some embodiments, the olefin from the pyrolysis process and the olefin from the oxygenate to olefin process are separated in a common separation zone to recover ethylene and/or propylene.

This integration of the pyrolysis process and the oxygenate to olefin process reduces the capital cost of the unit because of the common separation zone. It also reduces the overall size of the unit for a fixed olefin capacity.

Figure 1:
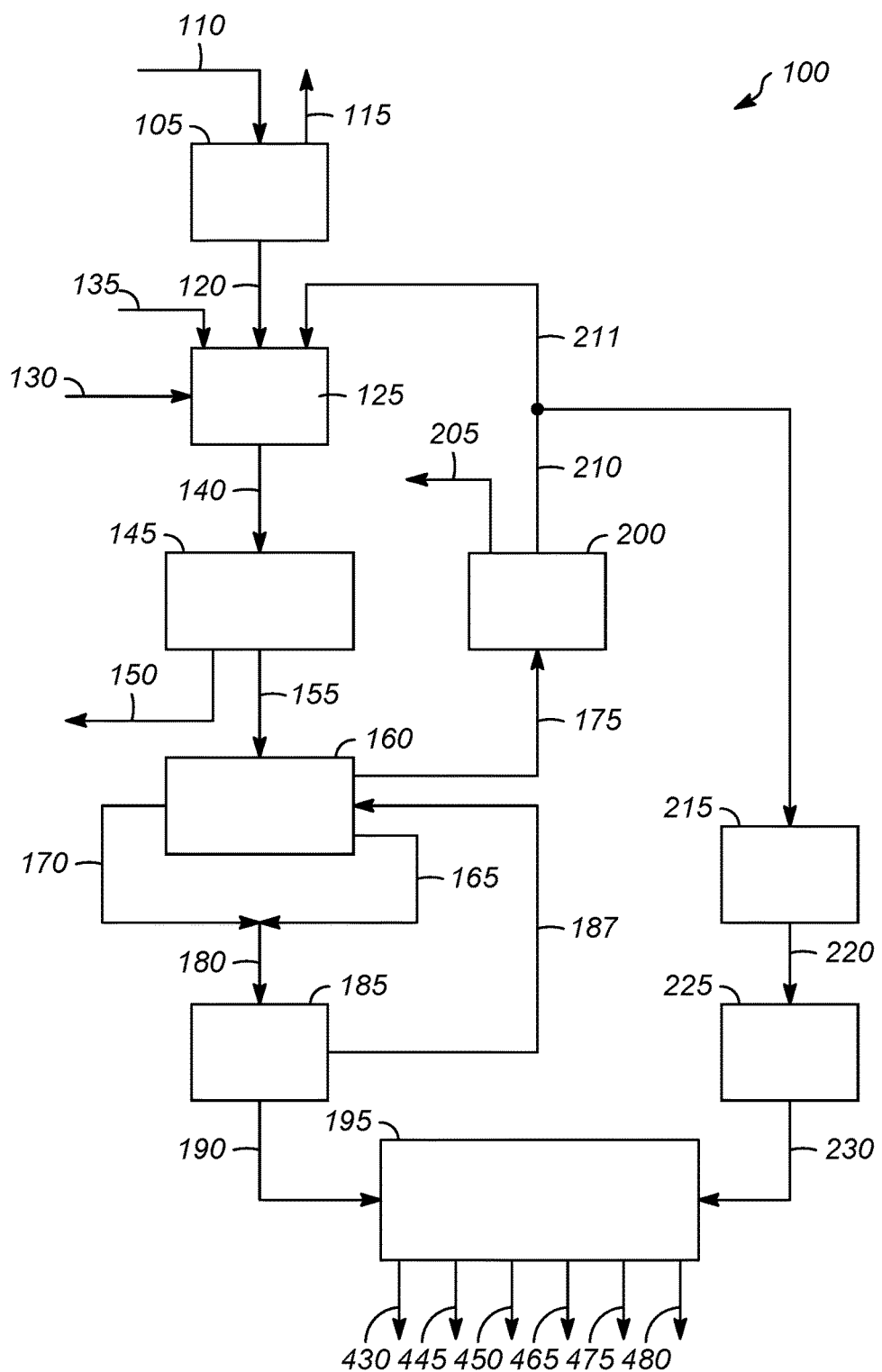
FIG. 1 is an illustration of one embodiment of a process of the present invention.

FIG. 1 illustrate one example of an integrated process 100 for converting a light hydrocarbon (e.g., methane) to an alkyne (e.g., acetylene) and then converting the alkyne (e.g., acetylene) to an olefin (e.g., ethylene), combined with the conversion of the carbon oxide and hydrogen byproduct gases into an oxygenate, optionally followed by conversion of the oxygenate into additional olefin.

First, the air separation unit 105 extracts oxygen from the air. The air separation unit 105 receives air via the air line 110, and generates the nitrogen rich stream 115 in which the oxygen content is less than that of air. The nitrogen rich stream 115 can be vented or reused. The air separation unit 105 also generates the oxygen rich stream 120 in which the oxygen content is greater than that of air. The air separation unit 105 can use processes known in the art such as cryogenic separation, membranes, or a pressure swing adsorption (PSA) process. In other embodiments, an oxygen containing stream 120 can be obtained from a pipeline or other sources.

In the process of FIG. 1, a hydrocarbon feedstock is converted into acetylene in a pyrolytic reactor 125. In one non-limiting example, the hydrocarbon feedstock is methane. The pyrolytic reactor 125 receives methane ($CH_4$) from methane line 130. The pyrolytic reactor 125 receives the oxidizer (oxygen) via oxygen rich stream 120. The pyrolytic reactor 125 receives the fuel (hydrogen or methane) via stream 135. A pyrolytic reactor outlet stream 140 produced by the pyrolytic reactor 125 may include acetylene, ethylene, hydrogen, methane, carbon monoxide, carbon dioxide, and carbon particulates.

Figure 2:
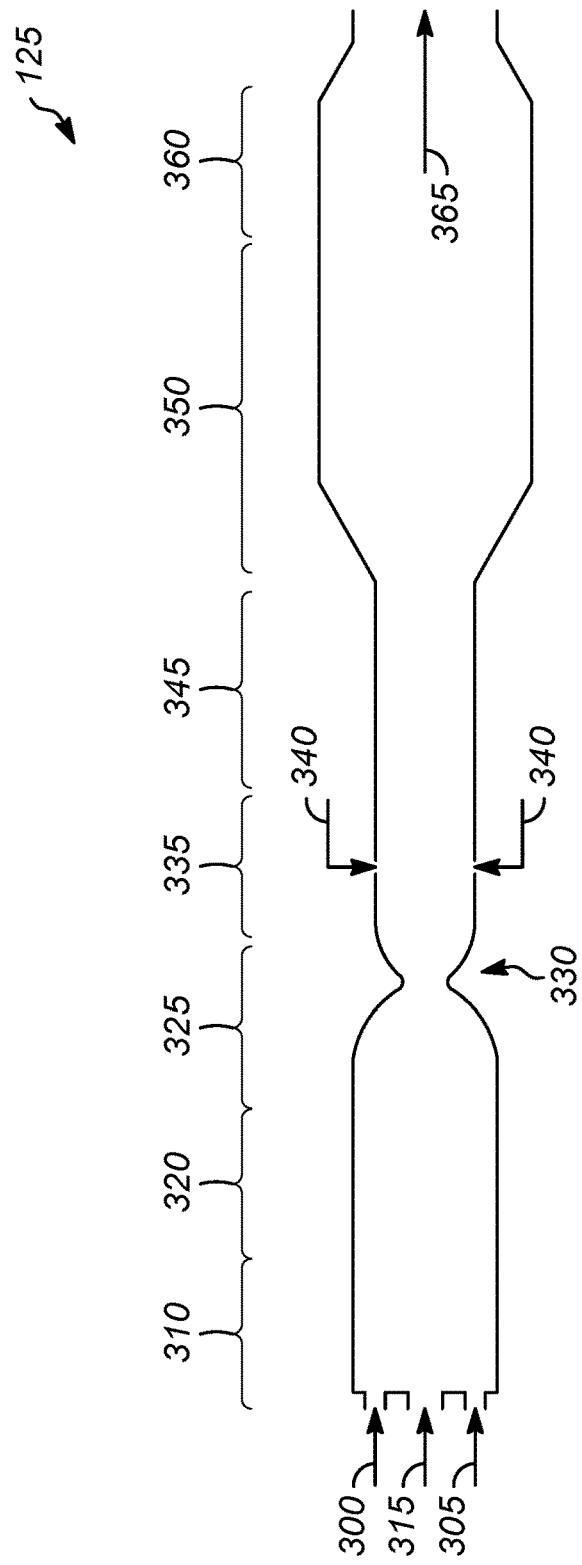
FIG. 2 is an illustration of one embodiment of a pyrolytic reactor useful in the present invention.

One example of a pyrolytic reactor 125 is illustrated in FIG. 2. The methane feedstock is heated to a temperature at which the formation of acetylene is thermodynamically favored over that of methane. Additional energy must be provided to the reaction mixture to satisfy the endothermic reaction for the formation of acetylene. After a residence time sufficient to result in the desired acetylene formation, the reaction mixture is quickly quenched to freeze the reaction in order to prevent the acetylene from cracking into hydrogen and carbon and reforming as methane. A fuel and oxidizer are combusted to create a high temperature (e.g., >1500 K) and high speed (e.g., >Mach 1) combustion gas, in order to favor acetylene formation. Next, a sufficient amount of reaction enthalpy is provided to satisfy the 377 kJ/mol required for the formation of acetylene. If additional energy is not provided, the endothermic nature of the acetylene formation may drive the temperature below 1500 K. Finally, the reaction mixture is quickly cooled at a rate faster than the rate at which the acetylene can decompose into hydrogen and carbon and subsequently reform as methane. This quick cooling process is sometimes referred to as "freezing" the reaction when the amount of acetylene is high. It is desirable to initiate the freezing step at the stage of maximum acetylene formation (i.e., the point of thermodynamic equilibrium) and to complete the freezing step as quickly as possible to prevent the decomposition of any acetylene.

A longitudinal cross section of an exemplary pyrolytic reactor 125 is shown in FIG. 2. In one embodiment, the pyrolytic reactor 125 is tubular (i.e., the transverse cross section is circular). The high temperatures necessary for the formation of acetylene as well as controlled residence time and rapid quenching can be achieved in the pyrolytic reactor 125. Fuel 300 and an oxidizer (e.g., oxygen) 305 are injected in the fuel injection zone 310 at the proximal end of pyrolytic reactor 125. In one embodiment, the fuel 300 and oxidizer 305 are heated to a temperature of 400° C. to 800° C., or to a temperature of 200° C. to 1000° C. in another embodiment. In one example embodiment, the fuel is hydrogen, the oxidizer is oxygen, and the ratio of hydrogen to oxygen is a 3/1 molar ratio.

In some embodiments, the fuel 300 and oxidizer 305 are mixed prior to injection into the fuel injection zone 310. In some embodiments, the fuel 300 and oxidizer 305 are injected into the fuel injection zone 310 and mixed by the turbulent conditions within the fuel injection zone 310. In some embodiments, steam or other diluents 315 is also injected into the fuel injection zone 310.

The fuel 300 and oxidizer 305 are combusted in the combustion zone 320. The resulting combustion gas stream is heated to a high temperature by the combustion reaction. In some embodiments, the temperature of the combustion gas stream is 2500 K to 3500 K in the combustion zone 320. In other embodiments, the temperature of the combustion gas stream reaches is 2000 K to 4000 K in the combustion zone 320.

The combustion zone 320 is operated at a pressure of 200 kPa to 1000 kPa (2 to 10 bar) in one embodiment. In other embodiments the combustion zone 320 is operated at a pressure of 120 kPa to 2000 kPa (1.2 bar to 20 bar). The pressure within the combustion zone 320 propels the combustion gas stream toward the distal end of the pyrolytic reactor 125 at high velocity. In some embodiments, the velocity of the combustion gas stream at the distal end of the combustion zone 320 is below supersonic speed (i.e., less than Mach 1).

The subsonic combustion gas stream enters the expansion zone 325 and flows through a convergent-divergent nozzle 330. The convergent-divergent nozzle 330 transforms a portion of the thermal energy in the combustion gas stream into kinetic energy, resulting in a sharp increase in velocity of the combustion gas stream. The velocity of the combustion gas stream transitions from subsonic (i.e., less than Mach 1) to supersonic (i.e., greater than Mach 1) within the expansion zone 325. In one embodiment, at the distal end of the expansion zone 325, the temperature of the combustion gas stream is 1500 K to 3000 K. In one embodiment, at the distal end of the expansion zone 325, the average velocity of the combustion gas stream (across a transverse cross section) is greater than Mach 1. In one embodiment, the average velocity of the combustion gas stream is about Mach 2 or above.

Feedstock is injected into the supersonic combustion gas stream in the feedstock injection zone 335. In one embodiment, the feedstock is injected at a temperature of 700 K to 1200 K. In one embodiment, feedstock is injected at a temperature of 300 K to 2000 K. In one embodiment, feed lines 340 supply the feedstock. In one embodiment designed to remove impurities such as sulfur and chloride species, natural gas is mixed with a hydrogen containing stream to produce a stream with 0 to 5 mol % hydrogen (or more) and heated to about 370° C. and fed to a set of swing reactors that contains a hydrodesulfurization catalyst (e.g., CoMo on alumina) and an $H_2S$ adsorbent (e.g., ZnO) downstream of the hydrogenation catalyst either in the same vessel or in a different vessel. The $H_2S$ resulting from hydrodesulfurization will react with the adsorbent. The same system will remove organic chlorides present in the natural gas feed. The reactor that is offline can be regenerated by methods known in the art for example by using air or steam. If the natural gas contains high levels of $H_2S$ (for example, higher than 20 ppm), another embodiment would be to treat the natural gas with known gas sweetening processes such as membrane processes, or solvent absorption with chemical or physical solvents in order to lower the $H_2S$ content of the natural gas to levels that are economical for the hydrosulfurization/adsorbent system.

The combined stream composed of the combustion gas stream and the feedstock stream enters mixing zone 345 where the combined stream is mixed as a result of the turbulent flow in the stream. In one embodiment, oblique or normal shockwaves can be used to assist the mixing.

In some embodiments, the mixing zone can be eliminated. One embodiment of a pyrolytic reactor without a mixing zone is described in U.S. Application No. 62/183,310 entitled "PYROLYTIC REACTOR AND METHOD OF USING", filed on even date herewith, which is incorporated herein by reference.

In some embodiments, the velocity of the mixed stream remains at supersonic velocities within the reaction zone 350. Shocks are created in the reaction zone 350 by adjusting the backpressure of the reactor. Shocks will reduce the velocity of the combined stream and converts a portion of kinetic energy into thermal energy. The combined stream is then reduced to subsonic flow and quenched in quenching zone 360.

In some embodiments, the velocity of the mixed stream transitions from supersonic to subsonic within the reaction zone 350. At this transition point, a shockwave is formed, which results in a nearly instantaneous increase in the pressure and temperature of the mixed stream. In various embodiments, the temperature of the mixed stream immediately upstream of the shock wave is about 1500 K to 2300 K, as compared to about 1600 K to 2800 K immediately downstream of the shockwave. The conditions in the mixed stream downstream of the shockwave are favorable to the formation of acetylene. Thus, the pyrolytic reactor 125 can be called a shock wave reactor (SWR).

In some embodiments, a shock train is formed at the point where the stream transitions from supersonic to subsonic flow. A shock train is a series of weak shock waves that propagate downstream from the supersonic to subsonic transition point. Whereas a single shockwave will heat the mixture nearly instantaneously (at the location of the shockwave), a shock train will heat the mixture more gradually. Each shock wave in the shock train will increase the temperature of the stream.

The mixed stream is increased to a temperature sufficient to favor the formation of acetylene and to provide enough energy to satisfy the endothermic reaction.

In one embodiment, the product stream exits the reaction zone 350 and enters the quenching zone 360 to rapidly cool the product stream. In one embodiment, the quenching zone 360 comprises at least one injection nozzle to spray the product stream with water. The product stream is removed at location 365.

In order to maintain steady state operation of the pyrolytic reactor 125 over a long period of time, the combustion zone 320 can be cooled. For example, a cooling jacket can be disposed over the reactor wall near the combustion zone 320, thereby forming a coolant channel. A coolant, such as water, can be introduced into the coolant channel. In one embodiment, the coolant flows in a direction opposite to that of the combustion gas stream in the reactor. The coolant effluent flows out of the coolant channel at an outlet.

Returning to FIG. 1, the pyrolytic reactor outlet stream 140 is fed into the quench unit 145 to cool the reactive mixture in the pyrolytic reactor outlet stream 140 rapidly. The quench unit 145 may be a separate unit, or it may be incorporated into the quenching zone of the pyrolytic reactor 125. A quench fluid (e.g., water) is sprayed into the pyrolytic reactor outlet stream 140, and the quench fluid prevents further reactions in the pyrolytic reactor outlet stream 140. The quench unit 145 also removes particulates (e.g., soot) via line 150. Outlet stream 155 from the quench unit 145 may include acetylene, ethylene, hydrogen, methane, carbon monoxide, and carbon dioxide.

In the compression and acetylene recovery zone 160, the outlet stream 155 is compressed. The majority of the compressed gas is contacted with a solvent that absorbs acetylene, and the solvent and acetylene exit the acetylene recovery zone 160 via stream 165. Suitable solvents include n-methyl-2-pyrrolidone, dimethylformamide, acetone, tetrahydrofuran, dimethylsulfoxide, monomethylamine, and combinations thereof. A minority of the compressed gas is conveyed via stream 170. Gas that does not absorb in the solvent (e.g., hydrogen, methane, carbon monoxide, and carbon dioxide) exits the acetylene recovery zone 160 as stream 175.

Streams 165 and 170 are combined in line 180 at the top of the hydrogenation reactor 185. In one non-limiting example configuration, stream 170 is the source of the hydrogen for the hydrogenation reaction. Alternatively, hydrogen can be supplied or supplemented by other sources via line 170. In one non-limiting example configuration, the hydrogenation reactor 185 uses a liquid phase selective hydrogenation process (SHP) in which the solvent is n-methyl-2-pyrrolidone (NMP). The absorbed acetylene and solvent are contacted with a catalyst. In one embodiment, the catalyst contains at least one Group VIII metal on an inorganic support. In one embodiment, palladium is one of the Group VIII metals. In one embodiment, the catalyst also contains at least one metal from Group IB, IIB, IIIA, IVA, IA and VIIB. The acetylene is converted to ethylene in the hydrogenation reactor 185. The solvent can be recycled to the acetylene recovery zone 160 in line 187.

Hydrogenation zone effluent 190 exits the hydrogenation reactor 185 and enters the product separation zone 195, which will be described in more detail below.

Stream 175 from the acetylene recovery zone 160, which may include hydrogen, methane, carbon monoxide, and carbon dioxide, can be fed to an optional carbon dioxide separation zone 200 to remove carbon dioxide. The carbon dioxide separation zone 200 can use an amine solvent, such as N-methyl diethanolamine, to absorb or otherwise separate $CO_2$ from the stream materials. A stripper (not shown) can be subsequently used to strip the absorbed $CO_2$ from the amine solvent, permitting the reuse of the stripped amine solvent. One physical solvent process for capturing the $CO_2$ stream is UOP's Selexol process. Carbon dioxide stream 205 exits the carbon dioxide separation zone 200.

Stream 210 from the carbon dioxide separation zone 200 may include hydrogen, methane, and carbon monoxide. Carbon dioxide may also be present if there is no carbon dioxide separation zone. A portion 211 of stream 210 can be recycled to the pyrolytic reactor 125, if desired. The rest of stream 210 is sent to a carbon oxide conversion zone 215 in which the carbon oxides and hydrogen are converted to an oxygenated product in a gas or liquid phase reactor containing a methanol synthesis catalyst.

For example, methanol is typically synthesized in the gas phase or liquid phase over a heterogeneous catalyst. The synthesis reactions employed on an industrial scale are as follows:

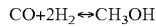
$$CO+2H_2 \leftrightarrow CH_3OH$$

or

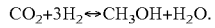
$$CO_2+3H_2 \leftrightarrow CH_3OH+H_2O.$$

The reaction from synthesis gas to oxygenates such as methanol is an exothermic reaction which is favored by low temperature and high pressure over a heterogeneous catalyst. The reactions which produce methanol exhibit a decrease in volume. As disclosed in U.S. Pat. No. 3,326,956, low-pressure methanol synthesis is based on a copper oxide-zinc oxide-alumina catalyst that typically operates at a nominal pressure of 5-10 MPa and temperatures ranging from about 150° C. to about 450° C. over a variety of catalysts, including $CuO/ZnO/Al_2O_3$, $CuO/ZnO/Cr_2O_3$, $ZnO/Cr_2O_3$, Fe, Co, Ni, Ru, Os, Pt, and Pd. Methanol yields from copper-based catalysts are generally over 99.5% of the converted $CO+CO_2$ present as methanol in the crude product stream. Water may be a by-product of the conversion of the synthesis gas to oxygenates.

The effluent 220 from the carbon oxide conversion zone 215 is sent to an oxygenate conversion zone 225 where the oxygenate is converted to an olefin. The most widely used oxygenate feed material is methanol.

In the oxygenate conversion zone 225, the oxygenate feed, e.g., methanol, is contacted with a molecular sieve catalyst, usually a silicoaluminophosphate (SAPO) molecular sieve catalyst, under conditions designed to convert the oxygenate feed into predominately light olefins. As used herein, references to "light olefins" are to be understood to generally refer to $C_2$ and $C_3$ olefins, i.e., ethylene and propylene, alone or in combination. In particular, the oxygenate conversion zone 225 produces or results in formation of an oxygenate conversion zone effluent 230 which generally comprises fuel gas hydrocarbons such as methane, ethane and propane, light olefins, and $C_{4+}$ hydrocarbons.

A non-limiting list of suitable SAPO molecular sieve catalysts includes SAPO-17, SAPO-18, SAPO-34, SAPO-35, SAPO-44, and mixtures thereof. The equipment and conditions with which this conversion reaction is conducted are well known to those skilled in the art and do not need to be detailed here. Numerous patents describe this process for various types of these catalysts including U.S. Pat. No. 3,928,483; U.S. Pat. No. 4,025,575; U.S. Pat. No. 4,252,479; U.S. Pat. No. 4,496,786; U.S. Pat. No. 4,547,616; U.S. Pat. No. 4,677,242; U.S. Pat. No. 4,843,183; U.S. Pat. No. 4,499,314; U.S. Pat. No. 4,447,669; U.S. Pat. No. 5,095,163; U.S. Pat. No. 5,191,141; U.S. Pat. No. 5,126,308; U.S. Pat. No. 4,973,792; and U.S. Pat. No. 4,861,938, the disclosures of which are incorporated herein by reference.

In general, the process for converting an oxygenate feedstock in the presence of a molecular sieve catalyst can be carried out in a variety of reactors, including as representative examples a fixed bed process, a fluidized bed process (includes a turbulent bed process), a continuous fluidized bed process, and a continuous high velocity fluidized bed process.

As noted, in addition to light olefins, the oxygenate conversion zone effluent 230 also typically includes methane, ethane, propane, dimethyl ether, $C_4$ olefins and saturates, $C_{5+}$ hydrocarbons, water and other hydrocarbon components in minor amounts.

The oxygenate conversion zone effluent 230 is sent to the product separation zone 195, along with hydrogenation zone effluent 190. The product separation zone 195 separates the desired products, ethylene and propylene, from any other components that may be present. The other components may include hydrogen, carbon dioxide, carbon monoxide, nitrogen, methane, or ethane as possible examples. The product separation zone 195 may utilize conventional separation methods for recovery of ethylene such as cryogenic distillation, pressure-swing adsorption, and membrane separation processes. It may include additional selective hydrogenation reactors.

Figure 3:
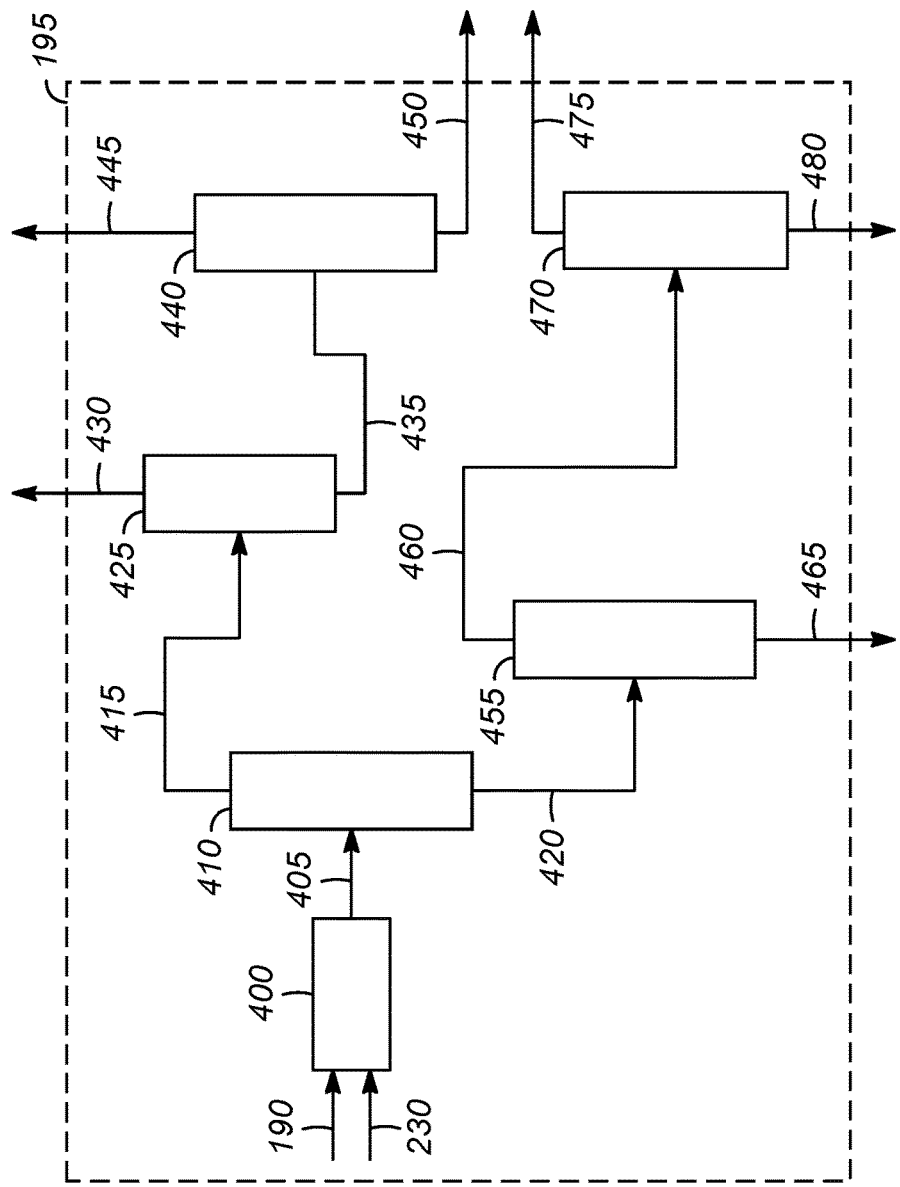
FIG. 3 is an illustration of one embodiment of a product separation zone useful in the present invention.

FIG. 3 illustrates one example of a product separation zone 195. The product separation zone 195 includes a drier unit 400 for drying the components in hydrogenation zone effluent 190 and oxygenate conversion zone effluent 230. The drier unit 400 typically includes one or more cryogenic fractionation columns. Olefin purification from hydrocarbon containing streams is well known to those skilled in the art. Typically, the gaseous effluent is compressed and then chilled and passed through a series of pressurized fractionators to separate the effluent into streams rich in its component parts, e.g., hydrogen, methane, ethane, propane, ethylene, propylene, and mixed $C_4$ hydrocarbon streams, as is known to those of ordinary skill in the art. Alternatively, other separation processes known to those skilled in the art, including, but not limited to, extractive distillation, selective membrane separation and/or molecular sieve separation also can be advantageously used. The present invention is not limited to any particular separation procedure or arrangement.

Although the order of fractionation can vary, FIG. 3 presents one suitable embodiment for fractionating the dried product stream 405. The dried product stream 405, or a select portion thereof, can be passed to a deethanizer column 410 where it is fractionated, such as by conventional distillation, to provide a deethanizer overhead stream 415 comprising $C_2$ and lighter hydrocarbons (i.e., $C_{2-}$ hydrocarbons, including methane, acetylene, ethane, ethylene, and possibly also some inert species ($N_2$, CO, etc.), and a deethanized $C_{3+}$ bottoms stream 420 comprising components enriched in compounds heavier than ethane, such as propylene, propane, mixed butenes and/or butane.

The deethanizer overhead stream 415 can be treated to remove acetylene (not shown) and ultimately is passed to a demethanizer column 425. In the demethanizer column 425, the $C_{2-}$ hydrocarbon product is fractionated, such as by conventional distillation, to provide a or fuel gas stream 430 predominantly comprising $C_{1-}$ hydrocarbons including methane, but also including some ethane, and ethylene (which can be separately recovered from the stream, for example, by known adsorption processes (not shown)), and a demethanizer bottoms stream 435 comprising predominately ethylene and ethane.

The demethanizer bottoms stream 435, or at least a portion thereof, is passed to a $C_2$-splitter 440. In the $C_2$-splitter 440, the demethanizer bottoms stream 435 is treated, e.g., is fractionated, such as by conventional distillation, to provide an overhead ethylene product stream 445 and a bottoms stream 450, principally composed of ethane. The ethane-containing bottoms stream 450, or a portion thereof can advantageously be recycled to the hydrocarbon pyrolytic reactor 125, or can alternatively be used as fuel.

The deethanized $C_{3+}$ bottoms stream 420 or at least a portion thereof, is passed to a depropanizer column 455. In the depropanizer column 455, the deethanized $C_{3+}$ bottoms stream 420 can be treated or fractionated, such as by conventional distillation, to produce a depropanizer overhead stream 460 comprising $C_3$ materials and a depropanized stream 465 generally comprising $C_{4+}$ components (a stream containing $C_{4+}$ hydrocarbons). At least a portion of the stream 465 containing $C_4$ hydrocarbons can be processed through an olefin cracking reactor (not shown) in order to increase the production of light olefins, particularly propylene.

The depropanizer overhead stream 460, or at least a portion thereof, is passed to a $C_3$-splitter 470. In some embodiments, the depropanizer overhead stream 460 may next undergo oxygenate removal (not shown) to remove any dimethyl ether (DME) and other trace oxygenates from the $C_3$-containing depropanizer overhead stream 460 before it is separated in the $C_3$-splitter 470. In the $C_3$-splitter 470, the depropanizer overhead stream 460 is treated, e.g., is fractionated, such as by conventional distillation, to provide an overhead propylene product stream 475 and a bottoms stream 480, generally composed of propane. The propane-containing bottoms stream 480, or a portion thereof can advantageously be recycled to the hydrocarbon pyrolytic reactor 125, or alternatively can be used as fuel.

Thus, the product separation zone 195 usually produces a fuel gas stream 430, an ethane stream 450, a propane stream 480, an ethylene product stream 445, a propylene product stream 475, and a stream 465 containing $C_{4+}$ hydrocarbons. The fuel gas stream 430 generally includes the majority of the methane and hydrogen that was present in the dry product stream. The fuel gas stream 430 optionally is burned as a fuel in one or more of the steps of the integrated process.

The ethylene product stream 445 and/or the propylene product stream 475 are suitable as feedstocks for the formation of polyethylene and/or polypropylene and/or other copolymers.

In order to maximize the production of light olefins from the stream 465 containing $C_{4+}$ hydrocarbons, this stream may subjected to selective hydrogenation to catalytically convert diolefins (e.g., butadiene) and acetylenes in the stream to butenes and passed to an olefin cracking reactor (not shown). Conditions and catalysts to employ in the selective hydrogenation reactor will be recognized by those skilled in the art.

As used herein, the term about means within 10% of the value, or within 5%, or within 1%.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

The invention claimed is:

1. A method of making light olefins comprising:
   combusting a fuel and an oxidizer in a combustion zone of a pyrolytic reactor to create a combustion gas stream;
   transitioning a velocity of the combustion gas stream from subsonic to supersonic in an expansion zone of the pyrolytic reactor;
   injecting a light hydrocarbon into the supersonic combustion gas stream to create a mixed stream including the light hydrocarbon;
   transitioning the velocity of the mixed stream from supersonic to subsonic in a reaction zone of the pyrolytic reactor to produce a reaction mixture comprising an alkyne, carbon oxide, and hydrogen;
   separating the reaction mixture in an absorber into an alkyne stream comprising the alkyne and a byproduct stream comprising the carbon oxide and the hydrogen;
   catalytically hydrogenating the alkyne in a hydrogenation zone to produce a product stream containing a first light olefin;
   treating the byproduct stream to convert at least a portion of the carbon oxide and the hydrogen to an oxygenated product in a carbon oxide conversion zone;
   treating the oxygenated product in an oxygenate conversion zone to convert at least a portion of the oxygenated product to produce an effluent comprising a second light olefin; and
   separating the first light olefin from the product stream and separating the second light olefin from the effluent in a product separation zone.

2. The method of claim 1 further comprising: combining at least a portion of the product stream containing the first light olefin with at least a portion of the oxygenate conversion zone effluent containing the second light olefin to form a mixture; and wherein separating the first light olefin from the product stream and separating the second light olefin from the effluent in the product separation zone comprises separating the first light olefin and the second light olefin from the mixture in the product separation zone.

3. The method of claim 1 wherein the second light olefin comprises at least one of ethylene and propylene.

4. The method of claim 1 wherein the carbon oxide comprises carbon monoxide and carbon dioxide, and further comprising: separating the carbon dioxide from the byproduct stream before treating the byproduct stream.

5. The method of claim 4 further comprising: converting at least a portion of the carbon dioxide to methane; and recycling the methane to the pyrolytic reactor.

6. The method of claim 1 wherein the byproduct stream further comprises a portion of the light hydrocarbon, and further comprising: separating the portion of the light hydrocarbon from the byproduct stream before treating the byproduct stream.

7. The method of claim 6 further comprising: recycling the portion of the light hydrocarbon to the pyrolytic reactor.

8. The method of claim 1 wherein the fuel is hydrogen, the oxidizer is oxygen, the light hydrocarbon is methane, the alkyne is acetylene, the first light olefin is ethylene, and the oxygenated product is methanol.

9. A method of making light olefins comprising:
   combusting a fuel and an oxidizer in a combustion zone of a pyrolytic reactor to create a combustion gas stream;
   transitioning a velocity of the combustion gas stream from subsonic to supersonic in an expansion zone of the pyrolytic reactor;
   injecting a light hydrocarbon into the supersonic combustion gas stream to create a mixed stream including the light hydrocarbon;
   transitioning the velocity of the mixed stream from supersonic to subsonic in a reaction zone of the pyrolytic reactor to produce a reaction mixture comprising an alkyne, carbon oxide, and hydrogen;
   separating the reaction mixture in an absorber into an alkyne stream comprising the alkyne and a byproduct stream comprising the carbon oxide and the hydrogen;
   catalytically hydrogenating the alkyne in a hydrogenation zone to produce a product stream containing a first light olefin;
   treating the byproduct stream to convert at least a portion of the carbon oxide and the hydrogen to an oxygenated product in a carbon oxide conversion zone;
   treating the oxygenated product in an oxygenate conversion zone to convert at least a portion of the oxygenated product to produce an effluent comprising a second light olefin; and
   separating the first light olefin from the product stream and separating the second light olefin from the effluent in a product separation zone.

10. The method of claim 9 further comprising: combining at least a portion of the product stream containing the first light olefin with at least a portion of the oxygenate conversion zone effluent containing the second light olefin to form a mixture; and wherein separating the first light olefin from the product stream and separating the second light olefin from the effluent in the product separation zone comprises separating the first light olefin and the second light olefin from the mixture in the product separation zone.

11. The method of claim 9 wherein the second light olefin comprises at least one of ethylene and propylene.

12. The method of claim 9 wherein the carbon oxide comprises carbon monoxide and carbon dioxide, and further comprising: separating the carbon dioxide from the byproduct stream before treating the byproduct stream.

13. The method of claim 12 further comprising: converting at least a portion of the carbon dioxide to methane; and recycling the methane to the pyrolytic reactor.

14. The method of claim 9 wherein the byproduct stream further comprises a portion of the light hydrocarbon, and further comprising: separating the portion of the light hydrocarbon from the byproduct stream before treating the byproduct stream.

15. The method of claim 14 further comprising: recycling the portion of the light hydrocarbon to the pyrolytic reactor.

16. The method of claim 9 wherein the fuel is hydrogen, the oxidizer is oxygen, the light hydrocarbon is methane, the alkyne is acetylene, the first light olefin is ethylene, and the oxygenated product is methanol.

* * * * *